US008236810B2

(12) United States Patent
Schoenafinger et al.

(10) Patent No.: US 8,236,810 B2
(45) Date of Patent: Aug. 7, 2012

(54) SUBSTITUTED 8-AMINOALKYLTHIOXANTHINES, AND THEIR USE AS INHIBITORS OF DIPEPTIDYL PEPTIDASE IV

(75) Inventors: Karl Schoenafinger, Alzenau (DE); Gerhard Jaehne, Frankfurt (DE); Elisabeth Defossa, Idstein (DE); Guenter Billen, Niedernhausen (DE); Christian Buning, Bonn (DE); Georg Tschank, Essenheim (DE); Ulrich Werner, Miehlen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 781 days.

(21) Appl. No.: 11/622,029

(22) Filed: Jan. 11, 2007

(65) Prior Publication Data

US 2007/0265284 A1    Nov. 15, 2007

Related U.S. Application Data

(63) Continuation of application No. PCT/EP2005/007821, filed on Jul. 19, 2005.

(30) Foreign Application Priority Data

Aug. 3, 2004  (DE) .......................... 10 2004 037 554

(51) Int. Cl.
*C07D 473/04* (2006.01)
*C07D 473/06* (2006.01)
*A61K 31/522* (2006.01)
*A61P 31/10* (2006.01)
*A61P 19/02* (2006.01)
*A61P 3/06* (2006.01)

(52) U.S. Cl. ........... 514/263.2; 514/263.31; 514/263.23; 514/263.33

(58) Field of Classification Search ................ 514/263.2, 514/263.31, 263.32, 263.33; 544/266
See application file for complete search history.

(56) References Cited

U.S. PATENT DOCUMENTS

| | | | |
|---|---|---|---|
| 2,688,618 A | | 9/1954 | Cooper et al. |
| 4,742,065 A | | 5/1988 | Klosa et al. |
| 5,290,801 A | * | 3/1994 | Higley et al. ................. 514/395 |
| 6,143,743 A | * | 11/2000 | Wilde et al. .................... 544/266 |
| 2007/0299090 A1 | * | 12/2007 | Schoenafinger et al. 514/263.33 |
| 2009/0018148 A1 | * | 1/2009 | Moureau et al. ......... 514/263.33 |
| 2009/0163545 A1 | * | 6/2009 | Goldfarb ........................ 514/312 |

FOREIGN PATENT DOCUMENTS

| | | |
|---|---|---|
| DE | 1005517 | 4/1957 |
| EP | 0430300 | 11/1990 |
| WO | WO 9205175 | 4/1992 |
| WO | WO 0063208 | 10/2000 |
| WO | WO 02/068420 | 9/2002 |
| WO | WO 2004048379 | 6/2004 |

OTHER PUBLICATIONS

Tsirkin Farmakol. i Toksikol 23 118-124 (1960).*
Blandine Laferrere et al., Effects of bombesin, of a new bombesin agonist (BIM187) and a new anfagonist (BIM189) on food intake in rats, in relation to cholecystokinin, European Journal of Pharmacology, (1992), vol. 215(1), pp. 23-28.
Corri Black et al., Meglitinide analogues for type 2 diabetes mellitus, The Cochrane Collaboration Review, (2007).
Kejha J et al., Iodinated Phenoxyalkyltheophyllines, Cesko-Slovenska Farmacie, (1966), pp. 2-4, vol. 15(1).
Renzo Cesato et al., Bombesin Receptor Antagonists May Be Preferable to Agonists for Tumor Targeting, The Journal of Nuclear Medicine, (2008), vol. 49(2), pp. 318-326.
Truta, Elena et al., The Effects Induced by 8-(4-R)-phenoxymethylxanthinic compounds on germination, plantie growth and mitosis in *Allium cepa* L., Analele Stiintifics ale Universitatii Al. I. Cuza din Iasi, Sectiunea II a: Genetica si Biologie Moleculara (2001), pp. 43-49, vol. 200) Chemical Abstract Service.
Krutovskikh, G.N., et. al., Radioprotective Properties of Mercaoticaffeine Derivatives, Khimiko-Farmatsevticheskii Zhurnal (1975) vol. 9, No. 4, pp. 21-23, (Abstract only).
1H-Purine-2, 6-Dione, 3,7-Dihydro-1, 3-Dimethyl-7-(Phenylmethyl)-8-[[2-(1-Piperidinyl) Ethyl] Thio] = (9CI) (CA Index Name), Chemical Abstracts Service Database Chemabs 'Online! XP002348284, (2001-2002).
Chemical Abstracts, vol. 54, abs. No. 25303d-e, dated Nov. 10, 1960.
Database Registry Copyright 2011 ACS on STN RN 570388-81-7, dated Aug. 21, 2003.
Database Registry Copyright 2011 ACS on STN RN 570368-48-8, dated Aug. 21, 2003.
Database Registry Copyright 2011 ACS on STN RN 536719-40-1, dated Jun. 24, 2003.

(Continued)

*Primary Examiner* — Mark Berch
(74) *Attorney, Agent, or Firm* — Serena Farquharson-Torres; Scully, Scott, Murphy & Presser, P.C.

(57) ABSTRACT

The invention 8-aminothioxanthines and the derivatives of formula I

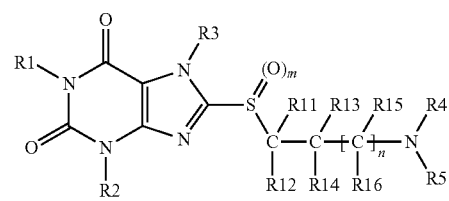

wherein the various R groups and substituents are comprised of a number of different ($C_1$-$C_{10}$)-alkyl, cycloalkyl, aryl, alkene, alkyne, etc. groups and derivatives thereof which are hereinafter more specifically defined for the treatment of metabolic disorders such as type-2 diabetes, hyperglycemia, arteriosclerotic diseases and the like.

4 Claims, No Drawings

OTHER PUBLICATIONS

Database Registry Copyright 2011 ACS on STN RN 476481-86-4, dated Dec. 17, 2002.
Database Registry Copyright 2011 ACS on STN RN 476480-43-0, dated Dec. 17, 2002.
Database Registry Copyright 2011 ACS on STN RN 460734-92-3, dated Oct. 11, 2002.
Database Registry Copyright 2011 ACS on STN RN 460734-82-1, dated Oct. 11, 2002.
Database Registry Copyright 2011 ACS on STN RN 460360-78-5, dated Oct. 10, 2001.
Database Registry Copyright 2011 ACS on STN RN 442865-20-5, dated Aug. 7, 2002.
Database Registry Copyright 2011 ACS on STN RN 442865-18-1, dated Aug. 7, 2002.
Database Registry Copyright 2011 ACS on STN RN 442865-08-9, dated Aug. 7, 2002.
Database Registry Copyright 2011 ACS on STN RN 442864-87-1, dated Aug. 7, 2002.
Database Registry Copyright 2011 ACS on STN RN 398995-33-0, dated Mar. 7, 2002.
Database Registry Copyright 2011 ACS on STN RN 398995-32-9, dated Mar. 7, 2002.
Database Registry Copyright 2011 ACS on STN RN 374771-03-6, dated Dec. 12, 2001.
Database Registry Copyright 2011 ACS on STN RN 335403-29-7, dated May 15, 2001.
Database Registry Copyright 2011 ACS on STN RN 335403-20-8, dated May 15, 2001.
Database Registry Copyright 2011 ACS on STN RN 335403-16-2, dated May 15, 2001.

* cited by examiner

SUBSTITUTED 8-AMINOALKYLTHIOXANTHINES, AND THEIR USE AS INHIBITORS OF DIPEPTIDYL PEPTIDASE IV

CROSS-REFERENCE TO RELATED APPLICATIONS

This application is a continuation of International Patent Application No. PCT/EP2005/007821 filed on Jul. 19, 2005 which is incorporated herein by reference in its' entirety which also claims the benefit of priority of German Patent Application No. 10 2004 037 554.2 filed on Aug. 3, 2004.

FIELD OF THE INVENTION

The present invention relates generally to compounds for the treatment of metabolic disorders such as type-2 diabetes, hyperglycemia, arteriosclerotic diseases and the like. Specifically, the present invention relates to compounds that inhibit the activity of dipeptidyl peptidase IV (DPP-IV) and are thus very suitable for lowering the blood glucose level. More specifically, the present invention relates to substituted 8-aminoalkylthioxanthines, their physiologically tolerated salts and functional derivatives and their therapeutic use as blood sugar-lowering agents among others.

BACKGROUND OF THE INVENTION

The enzyme dipeptidyl peptidase-IV (DPP-IV) inactivates a variety of bioactive peptides, including glucagon-like peptide-1 (GLP-1) and growth hormone releasing hormone (GHRH). Inhibiting DPP-IV in order to increase circulating GLP-1 is of interest as a treatment for Type II diabetes. Inactivation of DPP-IV may also increase circulating GHRH, potentially enhancing growth in domestic animals 8-(2-Aminoethylsulfanyl)-1,3,7-trimethyl-3,7-dihydropurine-2,6-dione has been described in the literature. This compound acts on the central nervous system (J. Med. Chem. (1966), 9 500-6). Inhibition of DPP-IV increases the circulating half-life of the incretin hormones GLP-1 and GIP, improving glucose tolerance in Type II diabetics. Complete inhibition of DPP-IV does not appear to be necessary: 2- to 3-fold increases in plasma concentrations of GLP-1 have been achieved in mice with inactivation of 84% to 96% of plasma DPP-IV Thus, there has been much interest in developing DPP-IV inhibitors for the treatment of Type II diabetes DPP-IV exists as both a membrane-spanning form present in cells throughout the body and a soluble circulating form. Both forms of DPP-IV have identical enzymatic activity and cleave a wide range of bioactive peptides in vitro, including hormones, neuropeptides, and chemokines. One potential regulatory role of DPP-IV is the inactivation of GHRH through cleavage of the active form, GHRH(1-44)-NH$_2$, to the N-terminally shortened inactive form, GHRH(3-44)-NH$_2$, While trypsin-like degradation of GHRH also occurs, in vitro studies using GHRH analogs designed to resist cleavage at the N-terminus have demonstrated that the primary degradation of GHRH is via DPP-IV. Substitution of Ala2 with Dali prevents DPP-IV proteolysis and administration of this analog increases GH release in swine up to 2-fold. The His1, Val2 analog of GHRH is also not degraded by DPP-IV in vitro, and it demonstrates increased plasma stability over native GHRH. GHRH analogs containing the His1, Val2 substitutions were 5.4- to 12.5-fold more potent than native GHRH in release of GH in swine. Thus, inhibition of DPP-IV in vivo may increase endogenous concentrations of GHRH and enhance GH secretion.

The present invention is based on the object of providing compounds which display a therapeutically utilizable blood glucose-lowering effect. -(2-Aminoethylsulfanyl)-1,3,7-trimethyl-3,7-dihydropurine-2,6-dione has been described in the literature. This compound is also known to act on the central nervous system (J. Med. Chem. (1966), 9 500-6).

SUMMARY OF THE INVENTION

The invention 8-aminothioxanthines and the derivatives of formula I

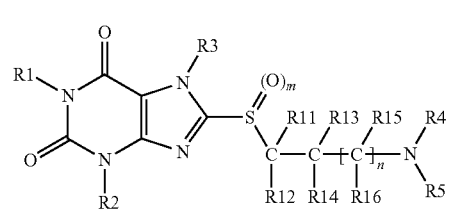

wherein the various R groups and sustituents are hereinafter defined for the treatment of metabolic disorders such as type-2 diabetes, hyperglycemia, arteriosclerotic diseases and the like.

DETAILED DESCRIPTION OF THE INVENTION

The invention 8-aminothioxanthines and the derivatives of the formula I

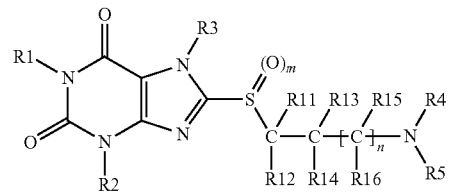

wherein R1, R2 and R3 are independently of one another selected from the group comprising H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, where the alkyl, cycloalkyl, alkenyl, alkynyl, aryl and heterocyclyl radicals may be substituted one or more times by F, Cl, Br, I, CN, NO$_2$, SH, SF$_5$, OH, (C$_1$-C$_6$)-alkyl, —CF$_3$, —OCF$_3$, —SCF$_3$, (C$_2$-C$_6$)-alkenyl, (C$_2$-C$_6$)-alkynyl, OR7, OP(O)(OR7)$_2$, NR7R8, NR7CONR7R8, COR7, OCOR7, OCOOR7, COOR7, CONR7R8, OCONR7R8, (C$_1$-C$_6$)-alkylene-OR7, (C$_1$-C$_6$)-alkylene-NR7R8, (C$_1$-C$_6$)-alkylene-NR7SO$_2$R7, (C$_1$-C$_6$)-alkylene-SR7, alkylene-S(O)R7, alkylene-CONR7R8, SR7, SOR7, SO$_2$R7, SO$_2$NR7R8, NR7SO$_2$R7, (C$_1$-C$_6$)-alkylene-(C$_3$-C$_{10}$)-cycloalkyl, (C$_1$-C$_6$)-alkylene-(C$_6$-C$_{10}$)-aryl, (C$_1$-C$_6$)-alkylene-heterocyclyl, (C$_3$-C$_{10}$)-cycloalkyl, (C$_6$-C$_{10}$)-aryl or heterocyclyl, where not all the radicals R1, R2 and R3 may simultaneously be hydrogen or methyl;

R7 and R8 are independently of one another selected from the group comprising H, (C$_1$-C$_6$)-alkyl, (C$_3$-C$_{10}$)-cycloalkyl, $(C_6-C_{10})$-aryl, heterocyclyl, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, $(C_1-C_4)$-alkylene-$(C_6-C_{10})$-aryl or $(C_1-C_4)$-alkylene-heterocyclyl;

R9 and R10 are independently of one another selected from the group comprising H, $(C_1-C_6)$-alkyl, $(C_1-C_6)$-alkylene-$(C_6-C_{10})$-aryl, $(C_1-C_6)$-alkylene-heterocyclyl;

R4 and R5 are independently of one another selected from the group comprising hydrogen, $(C_1-C_6)$-alkyl or $(C_3-C_8)$-cycloalkyl, where $(C_1-C_6)$-alkyl or $(C_3-C_8)$-cycloalkyl may be substituted by F, Cl, Br, I, CN, aryl, heterocyclyl, $NH_2$, $NH(C_1-C_6)$-alkyl, $N((C_1-C_6)$-alkyl$)_2$, OH, O$(C_1-C_6)$-alkyl, Oaryl, Oheteroaryl, S$(C_1-C_6)$-alkyl, S(O)$(C_1-C_6)$-alkyl, S(O)$_2$$(C_1-C_6)$-alkyl, where these alkyl groups may in turn be substituted by F, Cl, Br, I;

R11, R12, R13, R14, R15, R16 are independently of one another selected from the group comprising H, $(C_1-C_6)$-alkyl, aryl, heterocyclyl, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocyclyl, F, Cl, Br, I, CN, COOH, COO$(C_1-C_6)$-alkyl, CONH$_2$, CONH$(C_1-C_6)$-alkyl, CON$((C_1-C_6)$-alkyl$)_2$, $CF_3$, or two of the radicals R4, R5, R11, R12, R13, R14, R15, R16 together form a $(C_2-C_6)$-alkylene radical to which a $(C_6-C_{10})$-aryl radical or a $(C_6-C_{10})$-heterocyclyl radical may be fused, where the $(C_2-C_6)$-alkylene radical and the fused-on aryl radicals or heterocyclyl radicals may be substituted one or more times by F, Cl, Br, I, $OCF_3$, $CF_3$, CN, $(C_1-C_6)$-alkyl, aryl, heterocyclyl, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocyclyl, COOH, COO$(C_1-C_6)$-alkyl, CONH$_2$, CONH$(C_1-C_6)$-alkyl, CON$((C_1-C_6)$-alkyl$)_2$, OH, O—$(C_1-C_6)$-alkyl, O—$(C_3-C_6)$-cycloalkyl, S—$(C_1-C_6)$-alkyl, S—$(C_3-C_6)$-cycloalkyl, SO—$(C_1-C_6)$-alkyl, SO—$(C_3-C_6)$-cycloalkyl, $SO_2$—$(C_1-C_6)$-alkyl, $SO_2$—$(C_3-C_6)$-cycloalkyl, $SO_2$—$NH_2$, $SO_2$—NH—$(C_1-C_6)$-alkyl, $SO_2$—NH—$SO_2$—$(C_3-C_6)$-cycloalkyl may be substituted; where the aryl and heterocyclyl radicals may be substituted one or more times by F, Cl, Br, I, CN, $NO_2$, $SF_5$, OH, $(C_1-C_6)$-alkyl, —$CF_3$, —$OCF_3$, —$SCF_3$, $(C_2-C_6)$-alkenyl, $(C_2-C_6)$-alkynyl, O$(C_1-C_4)$-alkyl, $NH_2$, $NH(C_1-C_4)$-alkyl, $N((C_1-C_4)$-alkyl$)_2$, NR7CONH$(C_1-C_4)$-alkyl, CO$(C_1-C_4)$-alkyl, OCO$(C_1-C_4)$-alkyl, OCOO$(C_1-C_4)$-alkyl, COO$(C_1-C_4)$-alkyl, CONH$_2$, CONH$(C_1-C_4)$-alkyl, CON$((C_1-C_4)$-alkyl$)_2$, $(C_1-C_6)$-alkylene-O$(C_1-C_4)$-alkyl, $(C_1-C_6)$-alkylene-NH$(C_1-C_4)$-alkyl, $(C_1-C_6)$-alkylene-NH$_2$, $(C_1-C_6)$-alkylene-N$((C_1-C_4)$-alkyl$)_2$, $(C_1-C_6)$-alkylene-NHSO$_2$ $(C_1-C_4)$-alkyl, $(C_1-C_6)$-alkylene-S$(C_1-C_4)$-alkyl, alkylene-S(O)—$(C_1-C_4)$-alkyl, alkylene-CONH$_2$, alkylene-CONH$(C_1-C_4)$-alkyl, alkylene-CON$((C_1-C_4)$-alkyl$)_2$, S$(C_1-C_4)$-alkyl, SO$(C_1-C_4)$-alkyl, $SO_2$$(C_1-C_4)$-alkyl, $SO_2NH_2$, $SO_2NH(C_1-C_4)$-alkyl, $SO_2N((C_1-C_4)$-alkyl$)_2$, NR7SO$_2$$(C_1-C_4)$-alkyl, $(C_1-C_6)$-alkylene -$(C_3-C_{10})$-cycloalkyl, $(C_3-C_{10})$-cycloalkyl;

m is 0, 1, or 2;
n is 0 or 1;

and the physiologically tolerated salts thereof

Most preferably, the compounds of the present invention comprise compounds of formula I in which one or more R groups, substituents or radicals have the following meaning:

R1, R2 and R3 independently of one another are selected from the group comprising H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocyclyl, where the alkyl, cycloalkyl, alkenyl, alkynyl, aryl and heterocyclyl radicals may be substituted one or more times by F, Cl, Br, I, CN, $NO_2$, SH, $SF_5$, OH, $(C_1-C_6)$-alkyl, —$CF_3$, —$OCF_3$, —$SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, $SO_2$R7, $SO_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl, wherein not all the radicals R1, R2 and R3 may simultaneously be hydrogen or methyl;

R7, R8 are independently of one another selected from the group comprising H, $(C_1-C_6)$-alkyl, $(C_3-C_{10})$-cycloalkyl, $(C_6-C_{10})$-aryl, heterocyclyl, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_4)$-alkylene-$(C_6-C_{10})$-aryl or $(C_1-C_4)$-alkylene-heterocyclyl;

R9, R10 are independently of one another selected from the group comprising H, $(C_1-C_6)$-alkyl, $(C_1-C_6)$-alkylene-$(C_6-C_{10})$-aryl, $(C_1-C_6)$-alkylene-heterocyclyl;

R4, R5 are independently of one another selected from the group comprising H, $(C_1-C_6)$-alkyl or $(C_3-C_8)$-cycloalkyl, where $(C_1-C_6)$-alkyl or $(C_3-C_8)$-cycloalkyl may be substituted by the by F, Cl, Br, I, CN, aryl, heterocyclyl, $NH_2$, $NH(C_1-C_6)$-alkyl, $N((C_1-C_6)$-alkyl$)_2$, OH, O$(C_1-C_6)$-alkyl, Oaryl, Oheteroaryl, S$(C_1-C_6)$-alkyl, S(O)$(C_1-C_6)$-alkyl, S(O)$_2$$(C_1-C_6)$-alkyl;

R11, R12, R13, R14, R15, R16 are independently of one another selected from the group comprising H, $(C_1-C_6)$-alkyl or $(C_3-C_8)$-cycloalkyl, where $(C_1$ hydrogen, hydrogen, H, $(C_1-C_6)$-alkyl, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, F, Cl, Br, I, CN, COOH, COO$(C_1-C_6)$-alkyl, CONH$_2$, CONH$(C_1-C_6)$-alkyl, CON$((C_1-C_6)$-alkyl$)_2$, $CF_3$, or two of the radicals R4, R5, R11, R12, R13, R14, R15, R16 together form a $(C_2-C_6)$-alkylene radical, where the $(C_2-C_6)$-alkylene radical may be substituted one or more times by F, Cl, Br, I, CN, $NO_2$, $SF_5$, OH, $(C_1-C_6)$-alkyl, —$CF_3$, —$OCF_3$, —$SCF_3$, $(C_2-C_6)$-alkenyl, $(C_2-C_6)$-alkynyl, O$(C_1-C_4)$-alkyl, $NH_2$, $NH(C_1-C_4)$-alkyl, $N((C_1-C_4)$-alkyl$)_2$, NR7CONH$(C_1-C_4)$-alkyl, CO$(C_1-C_4)$-alkyl, OCO$(C_1-C_4)$-alkyl, OCOO$(C_1-C_4)$-alkyl, COO$(C_1-C_4)$-alkyl, CONH$_2$, CONH$(C_1-C_4)$-alkyl, CON$((C_1-C_4)$-alkyl$)_2$, $(C_1-C_6)$-alkylene-O $(C_1-C_4)$-alkyl, $(C_1-C_6)$-alkylene-NH$(C_1-C_4)$-alkyl, $(C_1-C_6)$-alkylene-NH$_2$, $(C_1-C_6)$-alkylene-N$((C_1-C_4)$-alkyl$)_2$, $(C_1-C_6)$-alkylene -NHSO$_2$$(C_1-C_4)$-alkyl, $(C_1-C_6)$-alkylene-S$(C_1-C_4)$-alkyl, alkylene-S(O)—$(C_1-C_4)$-alkyl, alkylene-CONH$_2$, alkylene-CONH$(C_1-C_4)$-alkyl, alkylene-CON$((C_1-C_4)$-alkyl$)_2$, S$(C_1-C_4)$-alkyl, SO$(C_1-C_4)$-alkyl, $SO_2$$(C_1-C_4)$-alkyl, $SO_2NH_2$, $SO_2NH(C_1-C_4)$-alkyl, $SO_2N((C_1-C_4)$-alkyl$)_2$, NR7SO$_2$$(C_1-C_4)$-alkyl, $(C_1-C_6)$-alkylene-$(C_3-C_{10})$-cycloalkyl, $(C_3-C_{10})$-cycloalkyl;

m is 0, 1, or 2;
n is 0 or 1;
and the physiologically tolerated salts thereof.

More preferably, the present invention comprises compounds of the formula I in which one or more R groups, substituents or radicals are further defined as:

R1, R2, R3 independently of one another are selected from the group comprising H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocyclyl, where the alkyl, cycloalkyl, alkenyl, alkynyl, aryl and heterocyclyl radicals which may be substituted one or more times by F, Cl, Br, I, CN, $NO_2$, SH, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene -NR7R8, $(C_1-C_6)$-alkylene-NR7SO$_2$R7, $(C_1-C_6)$-alkylene -SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl, where not all the radicals R1, R2 and R3 may simultaneously be hydrogen or methyl;

R7, R8 are independently of one another selected from the group comprising H, $(C_1-C_6)$-alkyl, $(C_3-C_{10})$-cycloalkyl, aryl, heterocyclyl, $(C_1-C_4)$-alkylene-$(C_6-C_{10})$-aryl or $(C_1-C_4)$-alkylene-heterocyclyl;

R4, R5 are independently of one another selected from the group comprising hydrogen, $(C_1-C_6)$-alkyl or $(C_3-C_8)$-cycloalkyl, where $(C_1-C_6)$-alkyl or $(C_3-C_8)$-cycloalkyl may be substituted by the by F, Cl, Br, I, CN, aryl, heterocyclyl, $NH_2$, $NH(C_1-C_6)$-alkyl, $N((C_1-C_6)$-alkyl)$_2$, OH, $O(C_1-C_6)$-alkyl, Oaryl, Oheteroaryl, $S(C_1-C_6)$-alkyl, $S(O)(C_1-C_6)$-alkyl, $S(O)_2(C_1-C_6)$-alkyl;

R11, R12, R13, R14, R15, R16 are independently of one another selected from the group comprising H, $(C_1-C_6)$-alkyl, and $(C_3-C_8)$-cycloalkyl, or two of the radicals R4, R5, R11, R12, R13, R14, R15, R16 together form a $(C_2-C_6)$-alkylene radical;

m is 0, 1 or 2;

n is 0;

and the physiologically tolerated salts thereof.

Most preferably, the present invention is comprised of compounds of formula I in which one or more of the R groups are defined as:

R1, R2, R3 are independently of one another selected from the group comprising $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, heterocyclyl, where the alkyl, cycloalkyl, alkenyl, alkynyl, aryl and heterocyclyl radicals my be substituted one or more times by F, Cl, Br, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, OR7, NR7R8, NR7CONR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R7, R8 are independently of one another selected from the group comprising H, $(C_1-C_6)$-alkyl, $(C_3-C_{10})$-cycloalkyl, aryl, heterocyclyl $(C_1-C_4)$-alkylene-$(C_6-C_{10})$-aryl or $(C_1-C_4)$-alkylene-heterocyclyl;

R4, R5 are both hydrogen;

R11, R12, R13, R14 are independently of one another selected from the group comprising H, $(C_1-C_6)$-alkyl or $C_3-C_7$-cycloalkyl;

m is 0;

n is 0;

and the physiologically tolerated salts thereof.

Most preferably, the present invention is comprised of formula I in which one or more R group radicals are defined as:

R1, R2 and R3 independently of one another are selected from the group comprising $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, heterocyclyl, where the alkyl, cycloalkyl, alkenyl, alkynyl, aryl and heterocyclyl radicals may be substituted one or more times by F, Cl, CN, $SF_5$, $(C_1-C_6)$-alkyl, $—CF_3$, $—OCF_3$, $—SCF_3$, $(C_2-C_4)$-alkenyl, $(C_2-C_4)$-alkynyl, OR7, NR7R8, NR7CONR7R8, COR7, COOR7, CONR7R8, $(C_1-C_4)$-alkylene-OR7, $(C_1-C_4)$-alkylene-NR7R8, $(C_1-C_4)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R7, R8 independently of one another are selected from the group comprising H, $(C_1-C_6)$-alkyl, $(C_3-C_{10})$-cycloalkyl, aryl, heterocyclyl, $(C_1-C_4)$-alkylene-$(C_6-C_{10})$-aryl or $(C_1-C_4)$-alkylene-heterocyclyl;

R4 and R5 are hydrogen;

R11, R12, R13, R14 are independently of one another selected from the group comprising H and $(C_1-C_4)$-alkyl;

m is 0;

n is 0;

and the physiologically tolerated salts thereof.

The present invention also relates to compounds of the formula I in the form of their racemates, racemic mixtures and pure enantiomers and to their diastereomers and mixtures thereof.

If the R groups, radicals and/or their substituents occur more than once in the compounds of the formula I, they may all, independently of one another, have the stated meanings and be identical or different.

Pharmaceutically acceptable salts are particularly suitable for because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, hexyl.

The alkyl radicals may be substituted one or more times by suitable groups such as, for example F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH(C_1$-$C_6$)-alkyl, $SO_2N[(C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO —($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH —CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO —NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-hetero-cycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N (($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N -(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O —($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkenyl radical means a straight-chain or branched hydrocarbon chain having two or more carbons and one or more double bonds, such as, for example, vinyl, allyl, pentenyl.

The alkenyl radicals may also be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH(C_1$-$C_6$)-alkyl, $SO_2N[(C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO —($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-
aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH —CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO —NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-hetero-cycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N (($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N -(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO -aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$) -alkyl)$_2$, N(heterocycle)-CO—N—($C_1$-$C_6$)-alkyl)$_2$, N(aryl)-CO—N(($C_1$-$C_6$)-alkyl) -aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O —($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkynyl radical means any straight-chain or branched hydrocarbon chain having two or more carbons and one or more triple bonds, such as, for example, ethynyl, propynyl, hexynyl. The alkynyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH(C_1$-$C_6$)-alkyl, $SO_2N[(C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO —($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-

$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl—CO—($C_1$-$C_6$)-alkyl, N($C_1$-$C_6$)-alkyl—COO—($C_1$-$C_6$)-alkyl, N($C_1$-$C_6$)-alkyl—CO-aryl, N($C_1$-$C_6$)-alkyl—CO-heterocycle, N($C_1$-$C_6$)-alkyl—COO-aryl, N($C_1$-$C_6$)-alkyl—COO-heterocycle, N($C_1$-$C_6$)-alkyl—CO—NH—($C_1$-$C_6$)-alkyl), N($C_1$-$C_6$)-alkyl—CO—NH-aryl, N($C_1$-$C_6$)-alkyl—CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An aryl R group or radical is defined as means a phenyl, naphthyl-, biphenyl-, tetrahydronaphthyl-, alpha- or beta-tetralon-, indanyl- or indan-1-on-yl radical. The aryl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH-CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl—CO—($C_1$-$C_6$)-alkyl, N($C_1$-$C_6$)-alkyl—COO—($C_1$-$C_6$)-alkyl, N($C_1$-$C_6$)-alkyl—CO-aryl, N($C_1$-$C_6$)-alkyl—CO-heterocycle, N($C_1$-$C_6$)-alkyl—COO-aryl, N($C_1$-$C_6$)-alkyl—COO-hetero-cycle, N($C_1$-$C_6$)-alkyl—CO—NH—($C_1$-$C_6$)-alkyl), N($C_1$-$C_6$)-alkyl—CO—NH-aryl, N($C_1$-$C_6$)-alkyl—CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

A cycloalkyl radical means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl radicals radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, (C2-C6)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH-CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl—CO—($C_1$-$C_6$)-alkyl, N($C_1$-$C_6$)-alkyl—COO—($C_1$-$C_6$)-alkyl, N($C_1$-$C_6$)-alkyl—CO-aryl, N($C_1$-$C_6$)-alkyl—CO-heterocycle, N($C_1$-$C_6$)-alkyl—COO-aryl, N($C_1$-$C_6$)-alkyl—COO-hetero-cycle, N($C_1$-$C_6$)-alkyl—CO—NH—($C_1$-$C_6$)-alkyl), N($C_1$-$C_6$)-alkyl—CO—NH-aryl, N($C_1$-$C_6$)-alkyl—CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-

CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O —(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

Heterocycle or heterocyclic radical means rings and ring systems which, apart from carbon, also comprise heteroatoms such as, for example, nitrogen, oxygen or sulfur. Also included in this definition are ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyi, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2, 4-thiadiazolyl, 1,2,5-thiadiazolyl, 1,3,4-thiadiazolyl, thienyl, triazolyl, tetrazolyl and xanthenyl.

Pyridyl compounds are selected from the group comprising 2-, 3- and 4-pyridyl. Thienyl comprises both 2- and 3-thienyl while furyl comprises both and 3-furyl.

Also included are the corresponding N-oxides of these compounds, for example, 1-oxy-2-, 3- or 4-pyridyl.

Also included are derivatives of these heterocycles which are fused as benzene rings one and optionally, more than one time.

The heterocyclic rings or heterocyclic R groups or radicals may be substituted one or more times by groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)-alkyl]$_2$, cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, O—CO —(C$_1$-C$_6$)-heterocycle; PO$_3$H$_2$, SO$_3$H, SO$_2$—NH$_2$, SO$_2$NH(C$_1$-C$_6$)-alkyl, SO$_2$N [(C$_1$-C$_6$) -alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO —(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N(C$_1$-C$_6$)-alkyl) (CH$_2$)$_n$-aryl, SO$_2$—N(C$_1$-C$_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$ where n may be 0-6, and the aryl radical or heterocyclic radical may be substituted up to twice by F, Cl, Br, OH, CF$_3$, NO$_2$, CN, OCF$_3$, O—(C$_1$-C$_6$)-alkyl, (C$_1$-C$_6$)-alkyl, NH$_2$; C(NH)(NH$_2$), NH$_2$, NH—(C$_1$-C$_6$)-alkyl, N((C$_1$-C$_6$)-alkyl)$_2$, NH(C$_1$-C$_7$)-acyl, NH —CO—(C$_1$-C$_6$)-alkyl, NH—COO— (C$_1$-C$_6$)-alkyl, NH—CO-aryl, NH—CO-heterocycle, NH—COO-aryl, NH—COO-heterocycle, NH—CO—NH— (C$_1$-C$_6$)-alkyl, NH—CO—NH-aryl, NH—CO—NH-heterocycle, N(C$_1$-C$_6$)-alkyl —CO—(C$_1$-C$_6$)-alkyl, N(C$_1$-C$_6$)-alkyl —COO—(C$_1$-C$_6$)-alkyl, N(C$_1$-C$_6$)-alkyl —CO-aryl, N(C$_1$-C$_6$)-alkyl —CO-heterocycle, N(C$_1$-C$_6$)-alkyl —COO-aryl, N(C$_1$-C$_6$)-alkyl —COO-hetero-cycle, N(C$_1$-C$_6$)-alkyl —CO—NH—(C$_1$-C$_6$)-alkyl), N(C$_1$-C$_6$)-alkyl —CO—NH-aryl, N(C$_1$-C$_6$)-alkyl —CO—NH-heterocycle, N((C$^1$-C$_6$)-alkyl)-CO—N—(C$_1$-C$_6$)-alkyl)$_2$, N((C$_1$-C$_6$)-alkyl)-CO—N ((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N -(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH— (C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$) -alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, and wherein the aryl radical or heterocyclic radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

The compound(s) of the formula (I) may also optionally be administered in combination with one or more additional active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula 1. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, lozenges, chewable tablets, each of which contain a defined amount of the compound of formula 1; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise lozenges and chewable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are: all antidiabetics mentioned in the Rote Liste 2004, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In another embodiment of the invention, the compounds of the formula I are administered in combination with a cholesterol absorption inhibitor such as, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531, U.S. Pat. No. 6,498,156.

In another embodiment of the invention, the compounds of the formula I are administered in combination with a peroxisome proliferator activated receptor (PPAR) gamma agonist, such as, for example, rosiglitazone, pioglitazone, JTT-501, GI 262570.

In yet another embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example as described in PCT/US 2000/11833, PCT/US 2000/11490 and DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245, 744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512). In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, In one embodiment of the invention, the compounds of the formula I are administered in combination with a lipoprotein lipase inhibitor.6.

In one embodiment of the invention, the compounds of the formula I are administered in combination with an ATP-citrate lyase inhibitor.

In one embodiment of the invention, the compounds of the formula I are administered in combination with a squalene synthetase inhibitor, In one embodiment of the invention, the compounds of the formula I are administered in combination with a lipoprotein(a) antagonist such as nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thia-zolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in EP 0912520 or PCT/EP 06749.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexyl -methyl}amide hydrochloride (CGP 71683A)), $MC_4$ agonists (e.g. 1-amino -1,2,3,4-tetrahydronaphthalene-2-carboxylic acid [2-(3a-benzyl-2-methyl -3-oxo-2,3,3a,4,6, 7-hexahydropyrazolo[4,3-c]pyridin-5-yl)-1-(4-chloro -phenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients mentioned in WO 02/28346, MSH (melanocyte-stimulating hormone) agonists, CCK-A agonists (e.g. {2-[4-(4-chloro-2,5-dimethoxyphenyl) -5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In a further embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (September-October 2001), 18(5), 230-6.) Caromax® is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

The compounds of the formula I are notable for beneficial effects on lipid and carbohydrate metabolism, in particular they lower the blood glucose level and are suitable for the treatment of type 2 diabetes, of insulin resistance, of dyslipidemias and of metabolic syndrome/syndrome X. The compounds are also suitable for the prophylaxis and treatment of arteriosclerotic manifestations. The compounds can be employed alone or in combination with other blood glucose-lowering active ingredients. The compounds act as DPP-IV (dipeptidyl peptidase IV) inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse.

They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

It will be appreciated that every suitable combination of the compounds of the invention with one or more of the aforementioned compounds and optionally one or more other pharmacologically active substances is regarded as falling within the protection conferred by the present invention.

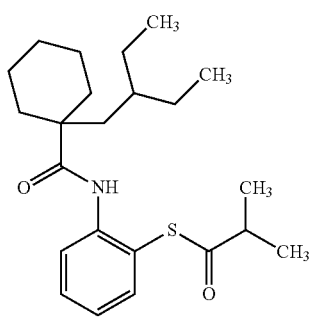
JTT-705

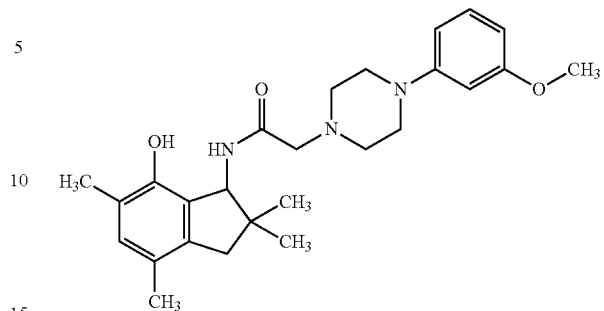
OPC-14117

SB-204990

NO-1886

Cl-1027

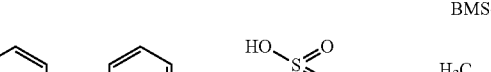
BMS-188494

GI 262570

-continued

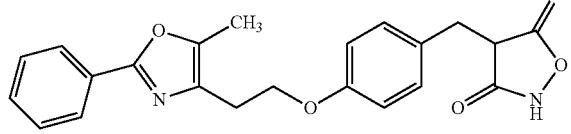

JTT-501

The compounds of the formula I can be prepared by reacting suitable starting materials of the formula II, in which R1, R2 and R3 have the meaning indicated above, and X is a leaving group such as chlorine, bromine, iodine, sulfonyloxide, sulfinyl, sulfoxyl, with a compound of the formula V, where appropriate in the presence of suitable bases, to give the compounds of the formula IV where X is a suitable leaving group such as, for example, chlorine, bromine, iodine, sulfonyloxide, sulfinyl or sulfoxyl.

Alternatively, compounds of the formula III in which R1, R2 and R3 have the meaning indicated above are reacted with alkylating agent of the formula VI to give the compounds of the formula IV, where X is a suitable leaving group such as, for example, chlorine, bromine, iodine, sulfonyloxide, sulfinyl or sulfoxyl.

In the cases where R4 or R5 is hydrogen, it may be expedient to employ the radical —NR4R5 in a form protected on the nitrogen function, and to eliminate the protective group again at a suitable point in the reaction. Such suitable protective groups and the methods for introducing and eliminating are known (see:Theodora W. Greene and Peter G. M. Wuts, Protective Groups in Organic Synthesis, 3rd edition, John Wiley & Sons, Inc., New York, 1999)

The thioether function in IV can then be oxidized by known methods to give the substances of the invention of the formula I in which n is a number 1 or 2.

The halogen compounds of the formula II can be obtained by known methods such as, for example, by halogenation of the corresponding H or OH compound (formula 2, X=H, OH). Suitable halogenating agents may be for example halogens such as chlorine and bromine, N-bromo-succinimide, phosphorus pentoxide or phosphorus oxichloride.

The compounds of the formula III can be obtained by reacting the halogen compounds of the formula II with suitable reagents such as, for example, hydrogen sulfide or thiourea by known methods.

The synthesis of compounds of the formula II and III is described many times in the literature (see Houben Weyl E9b/2, pp. 331 et seq.). They can be obtained for example starting from diaminopyrimidine derivatives or aminoimidazolecarboxamides by reaction with suitable reagents, and be converted by targeted chemical modifications such as hydrolysis, alkylation, halogenation into the desired starting compounds of the formula II or III.

The radicals R1 to R3 can be prepared by methods known per se by alkylating appropriate precursors, it being possible to vary the sequence. However, in some cases, they can also be introduced by the selection of appropriate precursors in the preparation of the xanthine structure.

The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

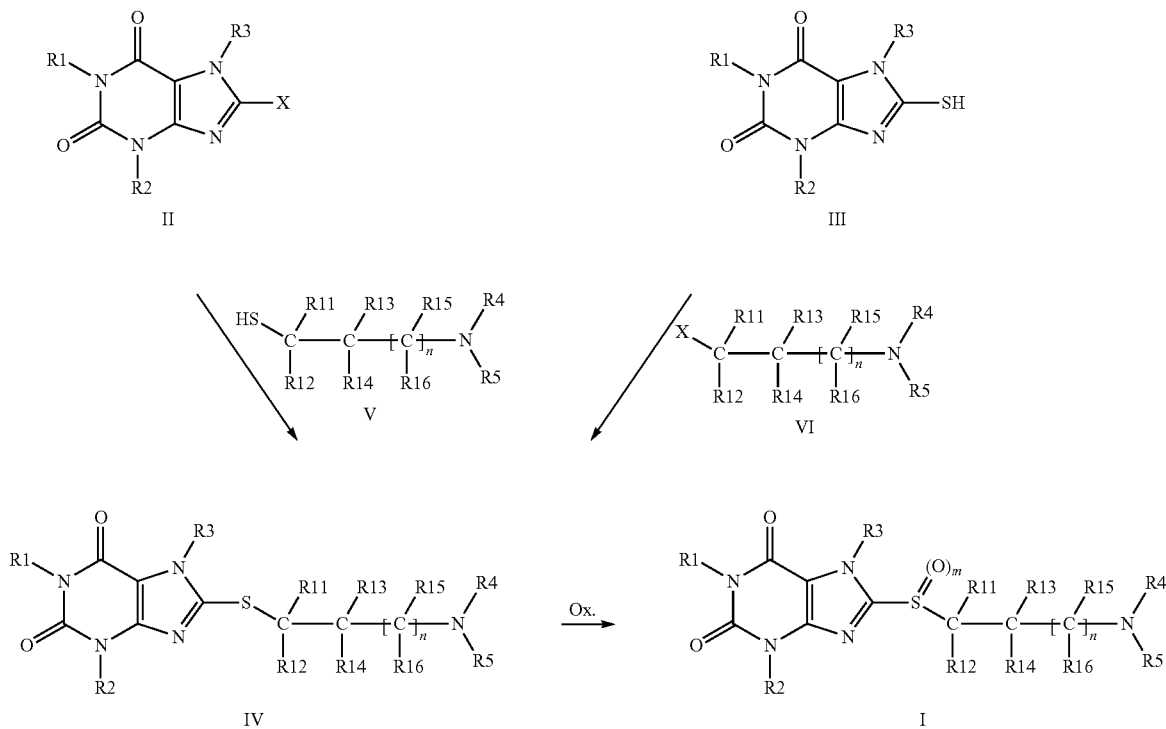

EXAMPLES

The following compounds as generically defined by formula and more specifically defined by the R groups and substituents set forth in Table 1

TABLE 1

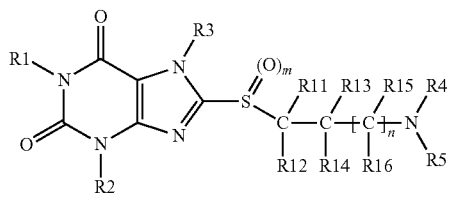

| Ex. | R1 | R2 | R3 | M | R4 | R5 | R11 | R12 | R13 | R14 | n | R15 | R16 |
|---|---|---|---|---|---|---|---|---|---|---|---|---|---|
| 1 | Ph—CO—CH$_2$— | CH$_3$ | —CH$_2$CH=C(CH$_3$)$_2$ | 0 | H | H | CH$_3$ | CH$_3$ | H | H | 0 | — | — |
| 2 | —CH$_2$CH$_3$ | CH$_3$ | —CH$_2$CH=C(CH$_3$)$_2$ | 0 | H | H | H | H | H | H | 0 | — | — |
| 3 | Ph—CO—CH$_2$— | CH$_3$ | —CH$_2$CH=C(CH$_3$)$_2$ | 0 | H | H | H | H | H | H | 0 | — | — |
| 4 | Ph—CO—CH$_2$— | CH$_3$ | —CH$_2$CH=C(CH$_3$)$_2$ | 0 | H (HCl salt) | H | CH$_3$ | CH$_3$ | H | H | 0 | — | — |
| 5 | H | CH$_3$ | —CH$_2$CH=C(CH$_3$)$_2$ | 0 | H | H | CH$_3$ | CH$_3$ | H | H | 0 | — | — |
| 6 | (F$_6$HC$_3$)OCH$_2$CH$_2$— | CH$_3$ | —CH$_2$CH=C(CH$_3$)$_2$ | 0 | H | H | CH$_3$ | CH$_3$ | H | H | 0 | — | — |
| 7 | Ph—CO—CH$_2$— | CH$_3$ | —CH$_2$CH=C(CH$_3$)$_2$ | 0 | 1,7,7-trimethylbicyclo-(2.2.1)hept-2-yl | H | H | H | H | H | 0 | — | — |

Assay and Results from Examples

The activity of the compounds was assayed as follows:

a) Measurement of the DPP-IV Activity:

Material:

DPP-IV from porcine kidney (Sigma Chemical Co, Munich DE)

H-Ala-Pro-AFC (Bachem Chemical Co, Weil am Rhein DE)

Assay Conditions:

Dipeptidyl peptidase-IV (DPP-IV) (1 mU/ml, final concentration)

H-Ala-Pro-AFC (15 μM, final concentration)

in Tris/HCl (40 mM, pH 7.4), total volume 0.2 ml

The reaction was carried out at room temperature for various times (typically 10 min) and stopped at the end of the reaction by adding 20 μl of ZnCl$_2$(1M). The H-Ala-Pro-AFC conversion was determined fluorimetrically by measuring the emission at 535 nm after excitation at 405 nm. When inhibitors were added, the added buffer volume was adapted so that a total volume of 200 μl was maintained for the assay mixture.

IC$_{50}$ values for inhibitors were determined by varying the inhibitor concentrations with the stated substrate concentration of 15 μM. Ki and Km values were found by appropriate variation of substrate concentration and inhibitor concentration as described (Dixon, M. and Webb, E. C.(1979) Enzymes, third edition, pp. 47-206, Academic Press). The values for Km, IC$_{50}$ and Ki were calculated using a commercially available software package (Leatherbarrow, R. J. (1992) GraFit Version 3.0, Erithacus Software Ltd. Staines, U.K.).

TABLE 2

| Biological activity | |
|---|---|
| Exemplary embodiment No. | IC-50 (nM) |
| 1 | 1.7 |
| 3 | 72 |
| 5 | 84 |
| 10 | 120 |
| 12 | 90 |
| 19 | 24 |
| 21 | 170 |
| 23 | 4.5 |
| 24 | 9.4 |
| 25 | 48 |
| 26 | 27 |

TABLE 2-continued

| Biological activity | |
|---|---|
| Exemplary embodiment No. | IC-50 (nM) |
| 36 | 21 |
| 42 | 16 |
| 43 | 30 |
| 63 | 14 |
| 64 | 7 |

It can clearly seen from table 2 that the compounds of formula I inhibit the activity of DPP-IV (dipeptidyl peptidase IV) and are thus very suitable for lowering the blood glucose level.

The preparation of some examples is described in detail below, and the other compounds of the formula I were obtained analogously:

Example 1

8-(2-Amino-1,1-dimethylethylsulfanyl)-3-methyl-7-(3-methylbut-2-enyl)-1-(2-oxo-2-phenylethyl)-3,7-dihydropurine-2,6-dione A mixture of 80 mg of 8-bromo-3-methyl-7-(3-methylbut-2-enyl)-1-(2-oxo-2-phenylethyl)-3,7-dihydropurine-2,6-dione, 53 mg of 1-amino-2-methyl-2-propanathiol hydrochloride, 2 ml of DMF and 77 μl of triethylamine was stirred at 80° C. for 6 hours.

After concentration, the oily residue was purified by column chromatography (silica gel, mobile phase: methylene chloride: methanol=9:1).

Yield: 25 mg m.p.: oil MS: M+1=456

The following were prepared analogously:

Example 2

8-(2-Aminoethylsulfanyl)-1-ethyl-3-methyl-7-(3-methylbut-2-enyl)-3,7-dihydropurine-2,6-dione m.p.: oil MS: M+1=338

Example 3

8-(2-Aminoethylsulfanyl)-3-methyl-7-(3-methylbut-2-enyl)-1-(2-oxo-2-phenylethyl)-3,7-dihydropurine-2,6-dione mp.: resin MS: M+1=428

Example 4

8-(2-Amino-1,1-dimethylethylsulfanyl)-3-methyl-7-(3-methylbut-2-enyl)-1-(2-oxo-2-phenylethyl)-3,7-dihydropurine-2,6-dione hydrochloride 100 mg of 8-(2-amino-1,1-dimethylethylsulfanyl)-3-methyl-7-(3-methylbut-2-enyl)-1-(2-oxo-2-phenylethyl)-3,7-dihydropurine-2,6-dione were dissolved in 2 ml of ethyl acetate and treated with excess solution of hydrogen chloride in ethyl acetate. After concentration in vacuo at room temperature, the residue was stirred with 5 ml of diisopropyl ether, and the product was filtered off with suction and dried in a vacuum.

Yield: 96 mg m.p.: MS: M+1=456

Example 5

8-(2-Amino-1,1-dimethylethylsulfanyl)-3-methyl-7-(3-methylbut-2-enyl)-3,7-dihydropurine-2,6-dione A mixture of 80 mg of 8-bromo-3-methyl-7-(3-methylbut-2-enyl)-3,7-dihydropurine-2,6-dione, 90 mg of 1-amino-2-methyl-2-propanethiol hydrochloride, 2 ml of DMF and 200 mg of cesium carbonate was stirred at 70° C. for 5 hours.

After concentration, the oily residue was purified by column chromatography (silica gel, mobile phase: methylene chloride: methanol =9:1).

Yield: 85 mg m.p.: oil MS: M+1=338

Example 6

8-(2-Amino-1,1-dimethylethylsulfanyl)-1-[2-(1,1,2,3,3,3-hexafluoropropoxy) -ethyl]-3-methyl-7-(3-methylbut-2-enyl)-3,7-dihydropurine-2,6-dione hydrochloride was obtained analogously starting from 8-bromo-1-[2-(1,1,2,3,3,3-hexafluoropropoxy)ethyl]-3-methyl-7-(3-methylbut-2-enyl)-3,7-dihydropurine-2,6-dione and was converted into the hydrochloride by reaction with a solution of hydrogen chloride in ethyl acetate.

m.p.: MS: M+1=532

Example 7

3-Methyl-7-(3-methylbut-2-enyl)-1-(2-oxo-2-phenylethyl)-8-[2-(1,7,7-trimethylbicyclo[2.2.1]hept-2-ylamino)ethylsulfanyl]-3,7-dihydropurine-2,6-dione hydrochloride was obtained analogously starting from 2-(1,7,7-trimethylbicyclo[2.2.1]hept-2-ylamino)ethanethiol hydrochloride in the presence of cesium carbonate and final treatment with hydrogen chloride.

m.p.: MS: M+1=564

Example 8

8-(2-Amino-1,1-dimethylethylsulfanyl)-1-(4-fluorobenzyl)-3-methyl-7-(3-methylbut-2-enyl)-3,7-dihydropurine-2,6-dione hydrochloride

MS: M+1=446

Example 9

2-[8-(2-Amino-1,1-dimethylethylsulfanyl)-3-methyl-7-(3-methylbut-2-enyl) -2,6-dioxo-2,3,6,7-tetrahydropurin-1-yl]-N-(4-chlorophenyl)acetamide hydrochloride

MS: M+1=505

Example 10

8-(2-Amino-2-methylpropylsulfanyl)-3-methyl-7-(3-methylbut-2-enyl)-1-(2-oxo-2-phenylethyl)-3,7-dihydropurine-2,6-dione

MS: M+1=456 a) 8-Mercapto-3-methyl-7-(3-methylbut-2-enyl)-1-(2-oxo-2-phenylethyl)-3,7-dihydropurine-2,6-dione 50 mg of 8-bromo-3-methyl-7-(3-methylbut-2-enyl)-1-(2-oxo-2-phenylethyl) -3,7-dihydropurine-2,6-dione were dissolved in 1 ml of dimethylformamide and, after addition of 24 mg of L-cysteine methyl ester hydrochloride and 37 mg of potassium carbonate, the mixture was heated with stirring at 90° C. for 1 hour. After cooling to room temperature, 10 ml of water were added, and the mixture was made weakly acidic with glacial acetic acid. A precipitate separated out on stirring and was filtered off and dried in a vacuum.

Yield: 40 mg m.p.: 182.7° C. MS: M+1=385 b) 8-(2-Amino-2-methylpropylsulfanyl)-3-methyl-7-(3-methylbut-2-enyl)-1-(2-oxo-2-phenylethyl)-3,7-dihydropurine-2,6-dione 30 mg of 8-mercapto-3-methyl-7-(3-methylbut-2-enyl)-1-(2-oxo-2-phenyl-ethyl)-3,7-dihydropurine-2,6-dione were introduced into 2 ml of dimethyl-formamide and, after addition of 37 mg of potassium carbonate, stirred for 15 minutes. Then 13.5 mg of mono(2-amino-2-methylpropyl)sulfate were added, and the mixture was stirred at 80° C. for 29 hours. The volatile fractions were removed in vacuum at 40° C., and the residue was purified by column chromatography (silica gel, mobile phase: methylene chloride: methanol =95:5).

Yield: 12 mg m.p.: resin MS: M+1=456

Example 11

8-(2-Amino-1,1-dimethylethylsulfanyl)-3-methyl-1-(2-oxo-2-phenylethyl)-7-(3,3,3-trifluoropropyl)-3,7-dihydropurine-2,6-dione hydrochloride

MS: M+1=484

Example 12

8-(2-Amino-1,1-dimethylethylsulfanyl)-1-(5-cyclopropyl-[1,3,4]thiadiazol-2-ylmethyl)-3-methyl-7-(3-methylbut-2-enyl)-3,7-dihydropurine-2,6-dione

MS: M+1=476

Example 13

8-(2-Amino-1,1-dimethylethyisulfanyl)-3-methyl-1,7-bis(3,3,3-trifluoro-propyl)-3,7-dihydropurine-2,6-dione hydrochloride

MS: M+1=462

Example 14

8-(2-Amino-1,1-dimethylethylsulfanyl)-1-cyclohexylmethyl-3-methyl-7-(3,3,3-trifluoropropyl)-3,7-dihydropurine-2,6-dione hydrochloride

MS: M+1=462

Example 15

8-(2-Amino-1,1-dimethylethylsulfanyl)-1-[3-(4-chlorophenyl)allyl]-3-methyl-7-(3,3,3-trifluoropropyl)-3,7-dihydropurine-2,6-dione hydrochloride

MS: M+1=516

Example 16

8-(2-Amino-1,1-dimethylethylsulfanyl)-1-(4-fluorobenzyl)-3-methyl-7-(3,3,3-trifluoropropyl)-3,7-dihydropurine-2,6-dione hydrochloride

MSW: M+1=474

Example 17

Methyl 2-amino-3-[3-methyl-7-(3-methylbut-2-enyl)-2,6-dioxo-1-(2-oxo-2-phenylethyl)-2,3,6,7-tetrahydro-1H-purin-8-ylsulfanyl]propionate hydrochloride

MS: M+1=486

Example 18

8-(2-Amino-1,1-dimethylethylsulfanyl)-7-(3-chloro-3-methylbutyl)-1-(5-fluorobenzothiazol-2-ylmethyl)-3-methyl-3,7-dihydropurine-2,6-dione hydrochloride

MS: M+1=539

Example 19

8-(2-Amino-1,1-dimethylethylsulfanyl)-1-(5-fluorobenzothiazol-2-ylmethyl)-3-methyl-7-(3-methylbut-2-enyl)-3,7-dihydropurine-2,6-dione

MS: M+1: 503

Example 20

3-Methyl-7-(3-methylbut-2-enyl)-1-(2-oxo-2-phenylethyl)-8-(pyrrolidin-2-yl-methylsulfanyl)-3,7-dihydropurine-2,6-dione hydrochloride

MS: M+1=468

Example 21

8-(2-Amino-1,1-dimethylethylsulfanyl)-3-methyl-7-(3-methylbut-2-enyl)-1-(5-methylisoxazol-3-ylmethyl)-3,7-dihydropurine-2,6-dione hydrochloride

MS: M+1=433

Example 22

8-(2-Amino-1,1-dimethylethylsulfanyl)-3-methyl-7-(3-methylbut-2-enyl)-1-(2,2,2-trifluoroethyl)-3,7-dihydropurine-2,6-dione hydrochloride

MS: M+1=420

Example 23

8-(2-Amino-1,1-dimethylethylsulfanyl)-3-ethyl-7-(3-methylbut-2-enyl)-1-(2-oxo-2-phenylethyl)-3,7-dihydropurine-2,6-dione

MS: M+1=470

Example 24

8-(2-Amino-1,1-dimethylethylsulfanyl)-3-cyclopropyl-7-(3-methylbut-2-enyl)-1-(2-oxo-2-phenylethyl)-3,7-dihydropurine-2,6-dione

MS: M+1=482

Example 25

8-(2-Amino-1,1-dimethylethylsulfanyl)-3-cyclopropyl-7-(3-methylbut-2-enyl)-1-phenethyl-3,7-dihydropurine-2,6-dione

MS: M+1=468

Example 26

8-(2-Amino-1,1-dimethylethylsulfanyl)-7-but-2-ynyl-3-methyl-1-(2-oxo-2-phenylethyl)-3,7-dihydropurine-2,6-dione

MS: M+1=440

Example 27

8-(2-Amino-1,1-dimethylethylsulfanyl)-7-but-2-ynyl-1-(3,3-dimethyl-2-oxo-butyl)-3-methyl-3,7-dihydropurine-2,6-dione

MS: M+1=420

Example 28

8-(2-Amino-1,1-dimethylethylsulfanyl)-3-ethyl-1-(3-hydroxy-3-methylbutyl)-7-(3-methylbut-2-enyl)-3,7-dihydropurine-2,6-dione

MS: M+1=438

Example 29

8-(2-Aminoethanesulfinyl)-3-methyl-7-(3-methylbut-2-enyl)-1-(2-oxo-2-phenylethyl)-3,7-dihydropurine-2,6-dione

MS: M+1=444

Example 30

8-(2-Amino-1,1-dimethylethylsulfanyl)-7-(2-chloro-4-fluorobenzyl)-1,3-dimethyl-3,7-dihydropurine-2,6-dione

MS: M+1=426

Example 31

8-(2-Amino-1,1-dimethylethylsulfanyl)-1,3-dimethyl-7-(2-oxo-2-phenylethyl)-3,7-dihydropurine-2,6-dione

MS: M+1=402

Example 32

8-(2-Amino-1,1-dimethylethylsulfanyl)-1-(1-benzyl-1H-imidazol-2-ylmethyl)-3-methyl-7-(3-methylbut-2-enyl)-3,7-dihydropurine-2,6-dione

MS: M+1=508

Example 33

8-(1-Aminomethylcyclohexylsulfanyl)-3-methyl-7-(3-methylbut-2-enyl)-1-(2-oxo-2-phenylethyl)-3,7-dihydropurine-2,6-dione

MS: M+1=496

70 mg (0.162 mmol) of 8-bromo-3-methyl-7-(3-methylbut-2-enyl)-1-(2-oxo-2-phenylethyl)-3,7-dihydropurine-2,6-dione were suspended with 57.3 mg (0.243 mmol) of 1-aminomethylcyclohexanethiol hydrochloride (prepared according to F. I. Carroll et al., J. Org. Chem 28, 1240-1243 (1963) or alternatively according to B. Roy et al., J. Org. Chem. 59, 7019-7026 (1994)) in 1 ml of dimethylformamide and, after addition of 158.6 mg (0.487 mmol) of cesium carbonate, stirred at 70° C. for 6 h. The reaction mixture was then concentrated in vacuo, dissolved in water/acetonitrile and purified by chromatography (Abimed; Purospher STAR RP18e, 10 μ; [acetonitrile: (water+0.05% trifluoroacetic acid)=5:95 (0 min) to 95:5 (40 min)]). 59 mg of 8-(1-aminomethylcyclohexylsulfanyl)-3-methyl-7-(3-methylbut-2-enyl)-1-(2-oxo-2-phenylethyl)-3,7-dihydropurine-2,6-dione were obtained. HPLC/MS [(acetonitrile+0.05% trifluoroacetic acid): (water+0.05% trifluoroacetic acid)=5:95 (0 min) to 95:5 (3 min)]: 496.24 (MH+), RT=1.55 min.

Example 34

2-[8-(2-Amino-1,1-dimethylethylsulfanyl)-1,3-dimethyl-2,6-dioxo-1,2,3,6-tetrahydropurine-7-ylmethyl]benzonitrile

MS: M+1=399

Example 35

8-(2-Amino-1,1-dimethylethylsulfanyl)-1,3-dimethyl-7-(3-phenylallyl)-3,7-dihydropurine-2,6-dione

MS: M+1=400

Example 36

8-(2-Amino-1,1-dimethylethylsulfanyl)-7-(3-methylbut-2-enyl)-1-(2-oxo-2-phenylethyl)-3-(2,2,2-trifluoroethyl)-3,7-dihydropurine-2,6-dione

MS: M+1=524

Example 37

8-(1-Aminomethylcyclohexylsulfanyl)-1-[2-(4-chlorobenzenesulfonyl)ethyl]-3-methyl-7-(3-methylbut-2-enyl)-3,7-dihydropurine-2,6-dione trifluoroacetate

MS: M+1=580

Example 38

(S)-8-(1-Aminomethylcyclohexylsulfanyl)-1-(2-fluoro-2-phenylethyl)-3-methyl-7-(3-methylbut-2-enyl)-3,7-dihydropurine-2,6-dione trifluoroacetate

MS: M+1=580

Example 39

8-(2-Amino-1,1-dimethylethylsulfanyl)-7-but-2-ynyl-1-(2-oxo-2-phenylethyl)-3-(2,2,2-trifluoroethyl)-3,7-dihydropurine-2,6-dione hydrochloride

MS: M+1=508

Example 40

8-(1-Aminomethylcyclohexylsulfanyl)-1-[2-(4-chlorophenylmethane-sulfonyl)ethyl]-3-methyl-7-(3-methylbut-2-enyl)-3,7-dihydropurine-2,6-dione trifluoroacetate

MS: M+1=594

Example 41

8-(1-Aminomethylcyclohexylsulfanyl)-7-benzyl-3-methyl-1-(2-oxo-2-phenyl-ethyl)-3,7-dihydropurine-2,6-dione trifluoroacetate

MS: M+1=518

Example 42

8-(2-Amino-1,1-dimethylethylsulfanyl)-1-[2-(2-chlorophenyl)-2-oxoethyl]-3-methyl-7-(3-methylbut-2-enyl)-3,7-dihydropurine-2,6-dione

MS: M+1=490

Example 43

8-(2-Amino-1,1-dimethylethylsulfanyl)-1-[2-(3-chlorophenyl)-2-oxoethyl]-3-methyl-7-(3-methylbut-2-enyl)-3,7-dihydropurine-2,6-dione

MS: M+1=490

Example 44

8-(2-Amino-1,1-dimethylethylsulfanyl)-1-[2-(4-chlorophenyl)-2-oxoethyl]-3-methyl-7-(3-methylbut-2-enyl)-3,7-dihydropurine-2,6-dione

MS: M+1=490

Example 45

8-(2-Amino-1,1-dimethylethylsulfanyl)-3-methyl-7-(3-methylbut-2-enyl)-1-(2-methyl-3-oxo-3-phenyl-propyl)-3,7-dihydropurine-2,6-dione

MS: M+1=484

Example 46

8-(2-Amino-1,-dimethylethylsulfanyl)-1-[2-(4-fluorobenzyl)-2H-tetrazol-5-ylmethyl]-3-methyl-7-(3-methylbut-2-enyl)-3,7-dihydropurine-2,6-dione

MS: M+1=528

Example 47

8-(2-Amino-1,1-dimethylethylsulfanyl)-1-[1-(4-fluorobenzyl)-1H-tetrazol-5-ylmethyl]-3-methyl-7-(3-methylbut-2-enyl)-3,7-dihydropurine-2,6-dione

MS: M+1=528

Example 48

8-(1-Aminomethylcyclohexylsulfanyl)-1-benzthiazol-2-ylmethyl-7-benzyl-3-methyl-3,7-dihydropurine-2,6-dione trifluoroacetate

MS: M+1=547

Example 49

8-(1-Aminomethylcyclohexylsulfanyl)-7-benzyl-3-methyl-1-(5-nitro-benzoxazol-2-ylmethyl)-3,7-dihydropurine-2,6-dione trifluoroacetate

MS: M+1=576

Example 50

8-(1-Aminomethylcyclohexylsulfanyl)-7-benzyl-1-(5-chlorobenzooxazol-2-yl-methyl)-3-methyl-3,7-dihydropurin-2,6-dione trifluoroacetate

MS: M+1=565

Example 51

8-(1-Aminomethylcyclohexylsulfanyl)-1-benzothiazol-2-ylmethyl-3-methyl-7-(3-methylbut-2-enyl)-3,7-dihydropurine-2,6-dione trifluoroacetate

MS: M+1=525

Example 52

8-(1-Aminomethylcyclohexylsulfanyl)-3-methyl-7-(3-methylbut-2-enyl)-1-(5-nitrobenzoxazol-2-ylmethyl)-3,7-dihydropurine-2,6-dione trifluoroacetate

MS: M+1=554

Example 53

8-(1-Aminomethylcyclohexylsulfanyl)-1-(5-chlorobenzoxazol-2-ylmethyl)-3-methyl-7-(3-methylbut-2-enyl)-3,7-dihydropurine-2,6-dione trifluoroacetate

MS: M+1=543

Example 54

8-(1-Aminomethylcyclohexylsulfanyl)-7-benzyl-1-(5-fluorobenzothiazol-2-yl-methyl)-3-methyl-3,7-dihydropurine-2,6-dione

MS: M+1=565

Example 55

8-(1-Aminomethylcyclohexylsulfanyl)-1-(5-fluorobenzothiazol-2-ylmethyl)-3-methyl-7-(3-methylbut-2-enyl)-3,7-dihydropurine-2,6-dione trifluoroacetate

MS: M+1=543

Example 56

[8-(2-Amino-1,1-dimethylethylsulfanyl)-3-methyl-7-(3-methylbut-2-enyl)-2,6-dioxo-2,3,6,7-tetrahydropurine-1-yl]acetonitrile

MS: M+1=377

Example 57

8-(1-Aminomethylcycloheptylsulfanyl)-7-benzyl-3-methyl-1-(2-oxo-2-phenyl-ethyl)-3,7-dihydropurine-2,6-dione trifluoroacetate

MS: M+1=532

Example 58

8-(1-Aminomethylcycloheptylsulfanyl)-3-methyl-7-(3-methylbut-2-enyl)-1-(2-oxo-2-phenylethyl)-3,7-dihydropurine-2,6-dione trifluoroacetate

MS: M+1=510

Example 59

2-[8-(2-Amino-1,1-dimethylethylsulfanyl)-3-methyl-7-(3-methylbut-2-enyl)-2,6-dioxo-2,3,6,7-tetrahydropurin-1-yl]acetamide

MS: M+1=395

Example 60

8-(1-Aminomethyl-1-ethylpropylsulfanyl)-3-methyl-7-(3-methylbut-2-enyl)-1-(2-oxo-2-phenylethyl)-3,7-dihydropurine-2,6-dione trifluoroacetate

MS: M+1=484

Example 61

8-(1-Aminomethyl-1-ethylpropylsulfanyl)-7-benzyl-3-methyl-1-(2-oxo-2-phenylethyl)-3,7-dihydropurine-2,6-dione trifluoroacetate

MS: M+1=506

Example 62

8-(2-Amino-1,1-dimethylethylsulfanyl)-3-methyl-7-(2-methyl-2H-tetrazol-5-ylmethyl)-1-(2-oxo-2-phenylethyl)-3,7-dihydropurine-2,6-dione

MS: M+1=484

Example 63

8-(1-Aminomethylcyclopentylsulfanyl)-7-benzyl-3-methyl-1-(2-oxo-2-phenyl-ethyl)-3,7-dihydropurine-2,6-dione trifluoroacetate

MS: M+1=504

Example 64

8-(1-Aminomethylcyclopentylsulfanyl)-3-methyl-7-(3-methylbut-2-enyl)-1-(2-oxo-2-phenylethyl)-3,7-dihydropurine-2,6-dione trifluoroacetate

MS: M+1=482

Example 65

8-(1-Aminomethylcyclooctylsulfanyl)-7-benzyl-3-methyl-1-(2-oxo-2-phenyl-ethyl)-3,7-dihydropurine-2,6-dione trifluoroacetate

MS: M+1=546

Example 66

8-(1-Aminomethylcyclooctylsulfanyl)-3-methyl-7-(3-methylbut-2-enyl)-1-(2-oxo-2-phenylethyl)-3,7-dihydropurine-2,6-dione trifluoroacetate

MS: M+1=524

Example 67

8-(2-Amino-1,1-dimethylethylsulfanyl)-3-methyl-7-(3-methylbut-2-enyl)-1-(5-phenyl-[1,3,4]oxadiazol-2-ylmethyl)-3,7-dihydropurine-2,6-dione

MS: M+1=496

Example 68

8-(2-Amino-1,1-dimethylethylsulfanyl)-3-methyl-7-(5-methyl-[1,3,4]oxa-diazol-2-ylmethyl)-1-(2-oxo-2-phenylethyl)-3,7-dihydropurine-2,6-dione

MS: M+1=484

Example 69

Ethyl 2-{2-[8-(2-amino-1,1-dimethylethylsulfanyl)-3-methyl-7-(3-methylbut-2-enyl)-2,6-dioxo-2,3,6,7-tetrahydropurin-1-yl]acetyl}benzoate

MS: M+1=528

Example 70

8-(2-Amino-1,1-dimethylethylsulfanyl)-3-methyl-1,7-bis(2,4,5-trifluoro-benzyl)-3,7-dihydropurine-2,6-dione

MS: M+1=558

Example 71

8-(2-Amino-1,1-dimethylethylsulfanyl)-1,7-bis(2,5-difluorobenzyl)-3-methyl-3,7-dihydropurine-2,6-dione

MS: M+1=522

Example 72

8-(2-Amino-1,1-dimethylethylsulfanyl)-7-(2-chlorobenzyl)-1,3-dimethyl-3,7-dihydropurine-2,6-dione

MS: M+1=408

Example 73

8-(2-Amino-1,1-dimethylethylsulfanyl)-7-(2-chloro-4-fluorobenzyl)-3-methyl-1-(2-oxo-2-phenylethyl)-3,7-dihydropurine-2,6-dione

MS: M+1=530

Example 74

8-(2-Amino-1,1-dimethylethylsulfanyl)-7-(2,5-difluorobenzyl)-3-methyl-1-(2-oxo-2-phenylethyl)-3,7-dihydropurine-2,6-dione

MS: M+1=514

Example 75

8-(2-Amino-1,1-dimethylethylsulfanyl)-3-methyl-1-(2-oxo-2-phenylethyl)-7-(2,4,5-trifluorobenzyl)-3,7-dihydropurine-2,6-dione

MS: M+1=532

Example 76

2-[8-(2-Amino-1,1-dimethylethylsulfanyl)-3-methyl-2,6-dioxo-1-(2-oxo-2-phenylethyl)-1,2,3,6-tetrahydropurin-7-ylmethyl]benzonitrile

MS: M+1=503

Example 77

8-(2-Amino-1,1-dimethylethylsulfanyl)-7-(4-fluorobenzyl)-1-methyl-3-(2,2,2-trifluoroethyl)-3,7-dihydropurine-2,6-dione trifluoroacetate

MS: M+1=460

Example 78

8-(2-Amino-1,1-dimethylethylsulfanyl)-7-(2-chlorobenzyl)-1-methyl-3-(2,2,2-trifluoroethyl)-3,7-dihydropurine-2,6-dione trifluoroacetate

MS: M+1=476

Example 79

8-(2-Amino-1,1-dimethylethylsulfanyl)-1-(2-morpholin-4-yl-2-oxoethyl)-7-oxazol-2-ylmethyl-3-(2,2,2-trifluoroethyl)-3,7-dihydropurine-2,6-dione trifluoroacetate

MS: M+1=546

Example 80

8-(2-Amino-1,1-dimethylethylsulfanyl)-7-(2-chlorobenzyl)-3-[2-(4-fluoro-phenyl)ethyl]-1-methyl-3,7-dihydropurine-2,6-dione trifluoroacetate

MS: M+1=516

Examples 81 to 83 Illustrate The Preparation Of The Starting Materials:

Example 81

8-Bromo-3-methyl-3,7-dihydropurine-2,6-dione 100 g of 3-methyl-3,7-dihydropurine-2,6-dione and 49 g of sodium acetate are suspended in 800 ml of glacial acetic acid and heated to an internal temperature of 90° C., and 33.3 ml of bromine are slowly added (about 3-4 hours). The suspension is then stirred at this temperature for 3 hours; the reaction is complete according to TLC (DCM/MeOH=10:1). The reaction solution is cooled and filtered with suction. The residue is washed with 100 ml of glacial acetic acid and 500 ml of water and dried in vacuum at 50° C.

Yield: 145 g m.p.: >300° C. (decomp.)

Example 82

8-Bromo-3-methyl-7-(3-methylbut-2-enyl)-3,7-dihydropurine-2,6-dione 50 g of 8-bromo-3-methyl-3,7-dihydropurine-2,6-dione are introduced into 900 ml of DMF, and 14.1 g of potassium carbonate are added. The suspension is heated to an internal temperature of 60° C., and 31.7 g of 1-bromo-3-methyl-2-butene are slowly added. The mixture is stirred at this temperature for 3 hours and then 1.2 l of water are added. The solid is filtered off with suction, thoroughly washed with water and dried in vacuo at 45° C.

Yield: 63.9 g m.p.: 223.3° C.

Example 83

8-Bromo-3-methyl-7-(3-methylbut-2-enyl)-1-(2-oxo-2-phenylethyl)-3,7-dihydropurine-2,6-dione 30 g of 8-bromo-3-methyl-7-(3-methylbut-2-enyl)-3,7-dihydropurine-2,6-dione, 20.6 g of phenacyl bromide and 25.4 g of potassium carbonate are introduced into 400 ml of DMF and heated at an internal temperature of 80° C. for 3 hours. The solution is cooled to about 50° C., and 400 ml of water are slowly added. The mixture is then stirred overnight, and the precipitated solid is filtered off with suction. After washing with water, the pale brown solid is recrystallized from 300 ml of isopropanol.

Yield: 39.7 g m.p.: 90.4°

What is claimed is:
1. A compound of the formula I,

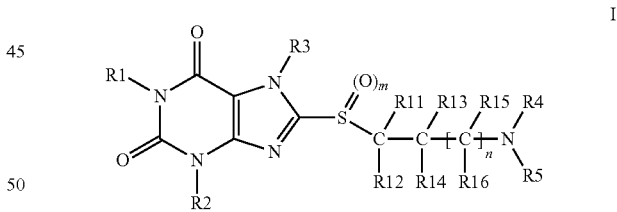

wherein one or more of the substituents are further defined as follows:

R1, R2, and R3 are independently of one another selected from the group consisting of $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, and heterocyclyl, where the alkyl, cycloalkyl, alkenyl, alkynyl, aryl and heterocyclyl radicals may be substituted one or more times by F, Cl, Br, CN, $NO_2$, $SF_5$, OH, $(C_1-C_6)$-alkyl, $-CF_3$, $-OCF_3$, $-SCF_3$, $(C_2-C_6)$-alkenyl, $(C_2-C_6)$-alkynyl, OR7, NR7R8, NR7CONR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, $SO_2$R7, $SO_2$NR7R8, NR7SO$_2$R7, $(C_1-C_6)$-alkylene-$(C_3-C_{10})$- cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle; and R7, R8 are independently of one another H, $(C_1-C_6)$-alkyl, $(C_3-C_{10})$-cycloalkyl, aryl, heterocyclyl, $(C_1-C_4)$-alkylene-$(C_6-C_{10})$-aryl or $(C_1-C_4)$-alkylene-heterocyclyl; and R4 and R5 are hydrogen; and R11, R12, R13 and R14 are independently of one another selected from the group consisting of H, $(C_1-C_6)$-alkyl and $C_3-C_7$-cycloalkyl;

m is 0 and;

n is 0;

or the physiologically tolerated salt thereof.

2. The compound as defined by formula I as recited in claim 1 wherein the substituents have the following meaning:

R1, R2, R3 are independently of one another selected from the group consisting of $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, and heterocyclyl, where the alkyl, cycloalkyl, alkenyl, alkynyl, aryl and heterocycle radicals may be substituted one or more times by F, Cl, CN, $SF_5$, $(C_1-C_6)$-alkyl, $-CF_3$, $-OCF_3$, $-SCF_3$, $(C_2-C_4)$-alkenyl, $(C_2-C_4)$-alkynyl, OR7, NR7R8, NR7CONR7R8, COR7, COOR7, CONR7R8, $(C_1-C_4)$-alkylene-OR7, $(C_1-C_4)$-alkylene-NR7R8, $(C_1-C_4)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle;

R7 and R8 are independently of one another selected from the group consisting of H, $(C_1-C_6)$-alkyl, $(C_3-C_{10})$-cycloalkyl, aryl, heterocyclyl, $(C_1-C_4)$-alkylene-$(C_6-C_{10})$-aryl and $(C_1-C_4)$-alkylene-heterocyclyl;

R4 and R5 are hydrogen;

R11, R12, R13 and R14 are independently of one another selected from the group consisting of H, and $(C_1-C_4)$-alkyl;

m is 0 and;

n is 0;

or the physiologically tolerated salt thereof.

3. A method for the treatment of type-2 diabetes comprising the administration of a compound of the formula I, wherein:

R1, R2 and R3 are independently of one another selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heteroyclyl, where the alkyl, cycloalkyl, alkenyl, alkynyl, and aryl wherein the heterocyclyl radicals may be substituted one or more times by F, Cl, Br, I, CN, NO$_2$, SH, SF$_5$, OH, $(C_1-C_6)$-alkyl, $-CF_3$, $-OCF_3$, $-SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocycle, with the proviso that R1=R2=R3=H and R1=R2=R3=methyl are excluded;

R7 and R8 are independently of one another selected from the group consisting of H, $(C_1-C_6)$-alkyl, $(C_3-C_{10})$-cycloalkyl, $(C_6-C_{10})$-aryl, heterocyclyl, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, $(C_1-C_4)$-alkylene-$(C_6-C_{10})$-aryl and $C_1$-C4)-alkylene-heterocyclyl;

R9 and R10 are independently of one another selected from the group consisting of H, $(C_1-C_6)$-alkyl, $(C_1-C_6)$-alkylene-$(C_6-C_{10})$-aryl, and $(C_1-C_6)$-alkylene-heterocycle;

R4 and R5 are independently of one another selected from the group consisting of hydrogen, $(C_1-C_6)$-alkyl [or] and $(C_3-C_8)$-cycloalkyl, where $(C_1-C_6)$-alkyl or $(C_3-C_8)$-cycloalkyl may be substituted by F, Cl, Br, I, CN, aryl, heterocyclyl, NH$_2$, NH$(C_1-C_6)$-alkyl, N$((C_1-C_6)$-alkyl)$_2$, OH, O$(C_1-C_6)$-alkyl, Oaryl, Oheteroaryl, S$(C_1-C_6)$alkyl, S(O)$(C_1-C_6)$-alkyl, S(O)$_2$$(C_1-C_6)$-alkyl, where these alkyl groups may in turn be substituted by F, Cl, Br, I;

R11, R12, R13, R14, R15 and R16 are independently of one another selected from the group consisting of H, $(C_1-C_6)$-alkyl, aryl, heterocyclyl, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocyclyl, F, Cl, Br, I, CN, COOH, COO$(C_1-C_6)$-alkyl, CONH$_2$, CONH$(C_1-C_6)$-alkyl, CON$((C_1-C_6)$-alkyl)$_2$, and CF$_3$, or two of the radicals R4, R11, R12, R13, R14, R15, R16 together form a $(C_2-C_6)$-alkylene radical to which a $(C_6-C_{10})$-aryl radical or a $(C_6-C_{10})$-heterocyclyl radical may be fused, where the $(C_2-C_6)$-alkylene radical and the fused-on aryl radicals or heterocyclyl radicals may be substituted one or more times by F, Cl, Br, I, OCF$_3$, CF$_3$, CN, $(C_1-C_6)$-alkyl, aryl, heterocyclyl, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heteroclyl, COOH, COO$(C_1-C_6)$-alkyl, CONH$_2$, CONH$(C_1-C_6)$-alkyl, CON$((C_1-C_6)$-alkyl)$_2$, OH, O-$(C_1-C_6)$-alkyl, O-$(C_3-C_6)$-cycloalkyl, S-$(C_1-C_6)$-alkyl, S-$(C_3-C_6)$-cycloalkyl, SO-9C$_1$-C$_6$)-alkyl, SO-$(C_3-C_6)$-cycloalkyl, SO$_2$-$(C_1-C_6)$-alkyl, SO$_2$-$(C_3-C_6)$-cycloalkyl, SO$_2$,-NH$_2$, SO$_2$,-NH-$(C_1-C_6)$-alkyl, SO$_2$-NH-SO$_2$-$(C_3-C_6)$-cycloalkyl; where the aryl and heterocyclyl radicals may be substituted one or more times by F, Cl, Br, I, CN, NO$_2$, SF$_5$, OH, $(C_1-C_6)$-alkyl, $-CF_3$, $-OCF_3$, $-SCF_3$, $(C_2-C_6)$-alkenyl, $(C_2-C_6)$-alkynyl, O$(C_1-C_4)$-alkyl, NH$_2$, NH$(C_1-C_4)$-alkyl, N$((C_1-C_4)$-alkyl)$_2$, NR7CONH$(C_1-C_4)$-alkyl, CO$(C_1-C_4)$-alkyl, OCO$(C_1-C_4)$-alkyl, OCOO$(C_1-C_4)$-alkyl, COO$(C_1-C_4)$-alkyl, CONH$_2$, CONH$(C_1-C_4)$-alkyl, CON$((C_1-C_4)$-alkyl)$_2$, $(C_1-C_6)$-alkylene-O$(C_1-C_4)$-alkyl, $(C_1-C_6)$-alkylene-NH$(C_1-C_4)$-alkyl, $(C_1-C_6)$-alkylene-NH$_2$, $(C_1-C_6)$-alkylene-N$((C_1-C_4)$-alkyl)$_2$, $(C_1-C_6)$-alkylene-NHSO$_2$$(C_1-C_4)$-alkyl, $(C_1-C_6)$-alkylene-S$(C_1-C_4)$-alkyl, alkylene-S(O)-(C1-C4)-alkyl, alkylene-CONH$_2$, alkylene-CONH$(C_1-C_4)$-alkyl, alkylene-CON$((C_1-C_4)$-alkyl)$_2$, S$(C_1-C_4)$-alkyl, SO$(C_1-C_4)$-alkyl, SO$_2$$(C_1-C_4)$-alkyl, SO$_2$NH$_2$, SO$_2$NH$(C_1-C_4)$-alkyl, $SO_2N((C_1-C_4)\text{-alkyl})_2$, $NR7SO_2(C_1\text{-}C4)\text{-alkyl}$, $(C_1-C_6)$-alkylene-$(C_3-C_{10})$-cycloalkyl, $(C_3-C_{10})$-cycloalkyl;

m is 0, 1, or 2; and n is 0 or 1;

or the physiologically tolerated salt thereof, to a patient in need thereof.

4. A method for the treatment of type-2 diabetes comprising the administration of a compound as recited in claim 2 to a patient in need thereof.

* * * * *